United States Patent
Araki et al.

(10) Patent No.: US 11,426,351 B2
(45) Date of Patent: Aug. 30, 2022

(54) PROCESS FOR PRODUCING A PHARMACEUTICAL COMPOSITION CONTAINING MICRO PARTICLES

(71) Applicant: SUNSTAR INC., Takatsuki (JP)

(72) Inventors: Mayo Araki, Takatsuki (JP); Rie Tanaka, Takatsuki (JP); Youko Takeda, Takatsuki (JP)

(73) Assignee: SUNSTAR INC., Takatsuki (JP)

( * ) Notice: Subject to any disclaimer, the term of this patent is extended or adjusted under 35 U.S.C. 154(b) by 0 days.

(21) Appl. No.: 16/727,183

(22) Filed: Dec. 26, 2019

(65) Prior Publication Data

US 2021/0196636 A1 Jul. 1, 2021

(51) Int. Cl.
*A61K 9/16* (2006.01)
*A61K 31/65* (2006.01)

(52) U.S. Cl.
CPC .......... *A61K 9/1682* (2013.01); *A61K 9/1611* (2013.01); *A61K 9/1617* (2013.01); *A61K 9/1635* (2013.01); *A61K 9/1652* (2013.01); *A61K 31/65* (2013.01)

(58) Field of Classification Search
None
See application file for complete search history.

(56) References Cited

U.S. PATENT DOCUMENTS

| | | | |
|---|---|---|---|
| 3,335,055 A | 8/1967 | Weidenheimer et al. | |
| 4,018,889 A | 4/1977 | Armstrong | |
| 6,589,511 B1 | 7/2003 | Shimizu | |
| 2008/0248124 A1 | 10/2008 | Eguchi et al. | |
| 2015/0125539 A1* | 5/2015 | Popov | A61K 9/5146 424/497 |

FOREIGN PATENT DOCUMENTS

| | | |
|---|---|---|
| GB | 1 592 053 | 7/1981 |
| JP | S52-90616 A | 7/1977 |
| JP | S53-94028 A | 8/1978 |
| JP | H02-34325 A | 8/1990 |
| JP | H07-29930 B2 | 4/1995 |
| WO | 98/41190 A1 | 9/1998 |

OTHER PUBLICATIONS

Dürig, et al., "Hydroxypropylcellulose polymer molecular weight: Influence on erodible modified release matrix system", Ashland, Pharmaceutical technology report, 2012, pp. 1-7 (Year: 2012).*

(Continued)

*Primary Examiner* — Kyung S Chang
(74) *Attorney, Agent, or Firm* — Buchanan Ingersoll & Rooney PC

(57) ABSTRACT

A pharmaceutical composition having consistently a desirable release rate is prepared by controlling the finally mixing time based on the molecular weight measured in the intermediate product. The pharmaceutical composition includes micro particles containing a polyhydric alcohol, a salt, a water-soluble polymer and a pharmaceutically active ingredient. The micro particles are dispersed in a matrix of a hydrophobic ingredient and an amphipathic ingredient.

9 Claims, 3 Drawing Sheets

(56) References Cited

OTHER PUBLICATIONS

Tewari et al., "Impact of molecular weight and molecular weight distribution of hypromellose in reducing drug release variability from erosion dependent matrix system", Ashland, Pharmaceutical technology report, 2012, pp. 1-4 (Year: 2012).*
Guar gum ([retrieved from on-line website: https://www.guargum.biz/guargum_chemical_structure.html, 2006, pp. 1-2]) (Year: 2006).*
International Search Report and Written Opinion dated Apr. 6, 2021, by the Japanese Patent Office in corresponding International Patent Application No. PCT/IB2020/001034. (12 pages).

* cited by examiner

PROCESS FOR PRODUCING A PHARMACEUTICAL COMPOSITION CONTAINING MICRO PARTICLES

TECHNICAL FIELD

The present invention relates to a process for producing a pharmaceutical composition. More specifically, the present invention relates to a process for producing a pharmaceutical composition containing micro particles which can stably contain an active ingredient unstable against water and can remain at an administered portion, thereby sustainedly release such active ingredient for a long period of time.

RELATED ART

Among active ingredients of pharmaceutical compositions such as antibiotics and anti-inflammatories, there are some active ingredients, which have a high efficacy, but are unstable and, therefore, are formulated into pharmaceutical compositions with limitation. For example, tetracycline and macrolide antibiotics are active ingredients having abroad antibacterial spectrum, but they are substances affected by water, heat or an additive and are easily denatured when they are formulated into compositions. Therefore, various techniques for stably formulating these antibiotics into pharmaceutical compositions have been previously studied.

For example, JP 52-90616 A discloses an aqueous solution for injection, aiming at stabilizing the tetracycline antibiotics such as oxytetracycline, doxycycline, tetracycline, chlortetracycline or salts thereof by chelating it with an alkaline earth metal compound such as a magnesium compound in an aqueous solution of 2-pyrrolidone. Moreover, JP 53-94028 A discloses a pharmaceutical composition, aiming at stabilizing oxytetracycline by incorporating into the composition an alkaline earth metal ion, polyvinylpyrrolidone and aliphatic amide and adjusting a pH of the composition to 5.0-7.5. Furthermore, U.S. Pat. No. 3,335,055 discloses a method for stabilizing tetracycline with a magnesium ion and a pyridine derivative such as isonicotinic acid amide, etc.

Moreover, JP H02-34325 B and JP H07-29930 B disclose a pharmaceutical composition which can stably contain one of tetracycline antibiotics, minocycline, and can exert the continuous effect of minocycline for a long period of time by formulating minocycline with a magnesium compound, a water-soluble polymer, a polyhydric alcohol, a methacrylate copolymer and a solubilizing agent.

When such pharmaceutical composition is simply produced according to one conventional procedure, water is mixed into the pharmaceutical composition and cannot be sufficiently removed by simply heating the composition at a high temperature for a long period of time because the water binds to a highly hydratable ingredient in the composition. In addition, a molecular chain of the polymer in the composition is sometimes cleaved, and that the ingredient in the composition is denatured due to a chemical reaction between the ingredients, etc.

For a periodontal pharmaceutical composition, if the pharmaceutical composition which cannot remain at an administered portion is administered to a periodontal disease portion, for example, a periodontal pocket, a concentration of the active ingredient in the periodontal pocket cannot be maintained for a long period of time due to a flow of saliva, foods, drinks, etc. in an oral cavity, even though a high concentration of the active ingredient temporarily remains at the periodontal pocket and a certain extent of treatment effects may be obtained.

U.S. 20080248124 discloses a process for producing a pharmaceutical composition containing an active ingredient which is unstable against water and providing sustained release for a long period of time. The process includes steps of: (i) mixing and heating a first phase, prepared by mixing ingredients (A) one or more of polyhydric alcohols and (B) one or more of salts, and a second phase containing an ingredient (C) one or more of water-soluble polymers under a reduced pressure, before evaporating substantially all water in the first phase by mixing and heating a mixture of first and second phases under a reduced pressure or after evaporating substantially all water in the first phase by mixing and heating the first phase under a reduced pressure; and (ii) adding a third phase containing an ingredient (D) one or more of active ingredients to the mixture to obtain the pharmaceutical composition. The pharmaceutical composition produced by this process can stably incorporate an active ingredient unstable against water and can remain at an administered portion, thereby, sustainedly release the active ingredient for a long period of time.

There is still an interest in producing such pharmaceutical composition exerting desirable release rate consistently.

SUMMARY

A pharmaceutical composition including micro particles dispersed in a matrix is prepared by:

i) obtaining a mixture comprising ingredients (A), (B) and (C) having a molecular weight M measured by gel permeation chromatography; and ii) mixing the mixture with a pharmaceutically active ingredient (D), a hydrophobic ingredient (E) and an amphipathic ingredient (F) at a temperature ranging from about 30° C. to 70° C. for a period of T minutes, thereby producing the pharmaceutical composition, wherein:

T satisfies following Equation I:

$$0.00136M - 230 < T < 0.00136M - 169 \qquad \text{Equation I;}$$

the ingredient (A) is a polyhydric alcohol;

the ingredient (B) is an inorganic magnesium, calcium or barium salt or a hydrate thereof; and the ingredient (C) is a water-soluble polymer.

DESCRIPTION OF PREFERRED EMBODIMENTS

Figure 1:
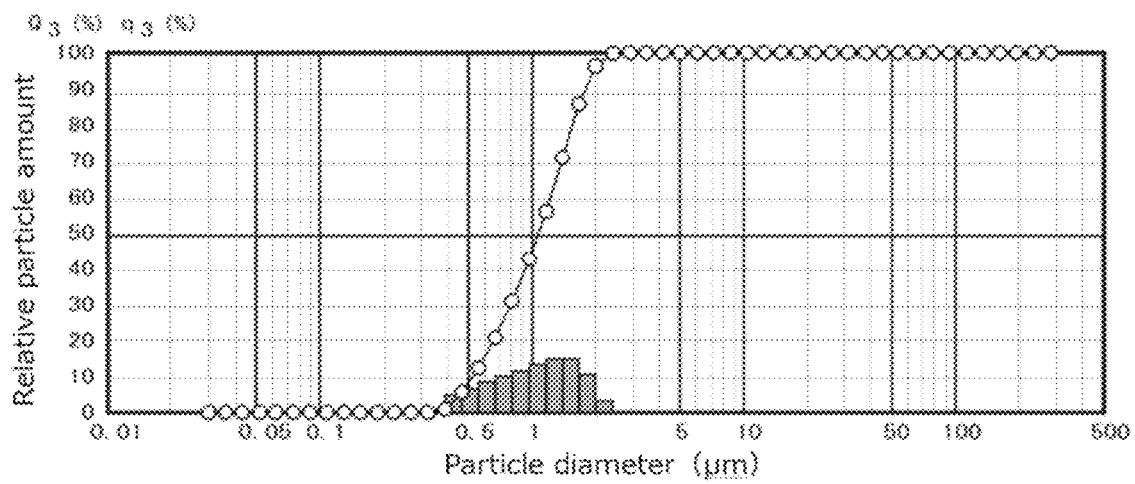
FIG. 1 is a graph showing a result of measurement of a particle diameter of Example 22.

In one embodiment, a process for producing a pharmaceutical composition includes: (i) obtaining a first mixture comprising ingredients (A), (B) and (C) having a molecular weight M measured by gel permeation chromatography; and (ii) mixing the first mixture with a pharmaceutically active ingredient (D), a hydrophobic ingredient (E) and an amphipathic ingredient (F).

Ingredient (A) is a polyhydric alcohol and preferably a water-soluble polymer. The polyhydric alcohol includes, but is not limited to, glycerin, ethylene glycol, diethylene glycol, propylene glycol, dipropylene glycol, hexylene glycol, 1,5-pentanediol, 1,3-butylene glycol, polyethylene glycol, etc. The polyhydric alcohols may be used alone or in a combination of two or more. In one embodiment, the ingredient (A) is glycerin, ethylene glycol or diethylene glycol. Glycerin is particularly preferable because it has a particularly high water content and a low irritation to a human body. Moreover, a pharmaceutical composition produced with glycerin provides excellent properties.

In one embodiment, the amount of the ingredient (A) is about 50% to about 85% by weight based on the total weight of the pharmaceutical composition. Preferably, the amount of the ingredient (A) is not lower than about 65% or about 70%, and not higher than about 80% by weight based on the total weight of the pharmaceutical composition. When the word "about" is used herein in connection with a numerical value, it is intended that the associated numerical value includes a tolerance of ±10% around the stated numerical value.

Ingredient (B) is a salt and preferably an inorganic salt. The useful salt includes, but is not limited to, an alkaline earth metal salt including a magnesium salt such as magnesium chloride, magnesium acetate, magnesium sulfate, magnesium nitrate, magnesium carbonate, magnesium gluconate, magnesium oxide, magnesium hydroxide, etc.; a calcium salt such as calcium chloride, calcium sulfate, calcium nitrate, calcium gluconate, calcium malate, calcium lactate, calcium oxide, calcium hydroxide, etc.; a barium salt such as barium chloride, barium sulfate, barium nitrate, etc. The hydrates of the above salts can also be used. The salts and hydrates thereof may be used alone or in a combination of two or more. Among them, the magnesium salts such as magnesium chloride, magnesium gluconate, magnesium acetate, magnesium sulfate, and magnesium nitrate or hydrates thereof are preferable because they suitably stabilize the active ingredient (D) unstable in water. In one embodiment, the ingredient (B) is magnesium chloride, magnesium gluconate, or a hydrate thereof. Magnesium chloride or a hexahydrate thereof, which is widely used in the pharmaceutical field, is particularly preferable.

The amount of the ingredient (B) is about 0.5% to about 10% by weight based on the total weight of the pharmaceutical composition. Preferably, the amount of the ingredient (B) is not lower than about 2% or about 3% and not higher than about 7% or about 6% by weight based on the total weight of the pharmaceutical composition. In one embodiment, the amount of the ingredient (B) is about 5% by weight based on the total weight of the pharmaceutical composition.

Ingredient (C) is a water-soluble polymer. The useful water-soluble polymer includes, but is not limited to, hydroxyethyl cellulose, hydroxymethyl cellulose (referred to as HEC), methylcellulose, hydroxypropyl cellulose, hydroxypropylmethyl cellulose, carboxymethylethyl cellulose, sodium carboxymethyl cellulose, sodium alginate, polyvinyl alcohol, polyvinylpyrrolidone, carrageenan, xanthan gum, locust bean gum, guar gum, tragacanth gum, starch, succinoglucan, etc. The water-soluble polymers may be used alone or in a combination of two or more. In one embodiment, the water-soluble polymer having a hydroxyl group is preferable. Cellulose derivatives are more preferable and hydroxyethyl cellulose is particularly preferable. In one embodiment, the ingredient (C) is hydroxyethyl cellulose, hydroxypropyl cellulose, hydroxypropylmethyl cellulose, or polyvinylpyrrolidone. In another embodiment, the ingredient (C) is hydroxyethyl cellulose or polyvinylpyrrolidone.

In an embodiment, the viscosity of a 2% aqueous solution of HEC is preferably 200-500, more preferably 250-400, when measured by Brookfield viscometer at 25° C.

The amount of the ingredient (C) is about 0.1% to about 20% by weight based on the total weight of the pharmaceutical composition. Preferably, the amount of the ingredient (C) is not lower than about 2% or about 3%, and not higher than about 7% or about 5% by weight based on the total weight of the pharmaceutical composition. In one embodiment, the amount of the ingredient (C) is about 4% by weight based on the total weight of the pharmaceutical composition.

In another embodiment, the amount of the ingredient (C) is about 0.2 parts to about 50 parts by weight, preferably about 1 parts to about 10 parts, by weight based on 100 parts by weight of the ingredient (A).

The active ingredient (D) includes an active ingredient unstable against water which becomes unstable in the presence of water. The phrase "an active ingredient unstable against water" as used herein means a compound that, when it is dissolved in or mixed with purified water at room temperature and stored at 25° C. for seven days, a ratio of an un-denatured ingredient is lowered to not greater than 95%, preferably to not greater than 90%. Examples of the active ingredient unstable against water include an anti-bacterial agent such as tetracycline, penicillin, carbapenem, cephem, monobactum, aminoglycoside and macrolide antibiotics; an anti-fungal agent such as polyene, azole, echinocandin and pyrimidine antibiotics; and an anti-inflammatory agent such as steroids and non-steroids, etc. The pharmaceutically acceptable salts of the above compounds can also be used. The active ingredients or pharmaceutically acceptable salts thereof may be used alone or in a combination of two or more. In a preferred embodiment, one or more tetracycline antibiotics, which are remarkably stabilized by a salt of bivalent metal ion, such as minocycline, doxycycline, tetracycline, oxytetracycline, chlortetracycline and pharmaceutically acceptable salts thereof can be used. In another preferred embodiment, minocycline or a pharmaceutically acceptable salt thereof, such as minocycline hydrochloride, can be used. Minocycline has a high affinity for the surface of the tooth and therefore remains in situ after release. Accordingly, a pharmaceutical composition containing minocycline can be used as a local therapeutic antibiotic agent for effective treatment of moderate to severe chronic periodontal disease.

The amount of the active ingredient (D) may vary depending upon a desired effect, and is generally about 0.1% to about 10.0% by weight based on the total weight of the pharmaceutical composition. Preferably, the amount of the active ingredient (D) is not lower than about 0.5%, about 0.7% or about 1%, and not higher than about 5%, about 3% or about 2.5% by weight based on the total weight of the pharmaceutical composition.

The ingredient (E) preferably is a methacrylate copolymer. Examples of the methacrylate copolymer include, but are not limited to, aminoalkyl methacrylate copolymer (a copolymer of methyl methacrylate with butyl methacrylate and dimethylaminoethyl methacrylate (for example, Eudragit®E, Pharma Polymers)), and aminoalkyl methacrylate copolymer (a copolymer of ethyl acrylate with methyl methacrylate and methacrylate ethyl trimethylammonium chloride (for example, Eudragit®RS, Pharma Polymers)), etc. The methacrylate copolymers may be used alone or in a combination of two or more.

The amount of the ingredient (E) is about 0.5% to about 10% by weight based on the total weight of the pharmaceutical composition. When the amount of the ingredient (E) is less than about 0.5% by weight, sustained-releasing of the active ingredient (D) becomes difficult. On the other hand, when the amount of the ingredient (E) is greater than about 10% by weight, a viscoelasticity of the composition becomes high and production of the pharmaceutical composition becomes difficult. Preferably, the amount of the ingredient (E) is not lower than about 0.5% or about 1%, and not higher than about 5% or about 3% by weight based on the total weight of the pharmaceutical composition. In one embodiment, the amount of the ingredient (E) is about 2% by weight based on the total weight of the pharmaceutical composition.

Amphipathic ingredient (F) is preferably an organic solvent. Examples of the organic solvent include, but are not limited to, an ester of a lower polyhydric alcohol with a lower fatty acid, such as triacetin, tributyrin, ethylene glycol diacetate, etc., an ester of a lower alcohol with a dicarboxylic acid, such as diethyl sebacate, diethyl phthalate, dibutyl phthalate, diisopropyl adipate, dibutyl succinate, etc. The organic solvents may be used alone or in a combination of two or more. As used herein, a "lower polyhydric alcohol" means a polyhydric alcohol containing 2-6 carbon atoms. A lower fatty acid and a lower alcohol each contain 1-6 carbon atoms.

The amount of the ingredient (F) is preferably about 5% to about 25% by weight based on the total weight of the pharmaceutical composition. When the amount of the ingredient (F) is within the range, a suitable pharmaceutical composition can be formed to provide desired sustained-releasing of the active ingredient (D). Preferably, the amount of the ingredient (F) is not lower than about 7% or about 10%, and not higher than about 15% or about 14% by weight based on the total weight of the pharmaceutical composition. In one embodiment, the amount of the ingredient (F) is about 12% by weight based on the total weight of the pharmaceutical composition.

In the case where an amount range of the aforementioned ingredients is defined herein, when the total amount of respective ingredients exceeds 100% by weight, of course, it should be understood that it means that respective ingredients are added in an amount within the defined range such that the total amount of the ingredients becomes not greater than 100% by weight.

In the pharmaceutical composition described herein, it is believed that the ingredient (A) (e.g., polyhydric alcohol) dissolves the ingredient (B) (e.g., salt) and forms micro particles containing the active ingredient (D) (e.g., minocycline) and the ingredient (B) with the ingredient (C) (e.g., water-soluble polymer). The ingredient (B) is used for stabilizing the active ingredient (D) unstable against water in the pharmaceutical composition. The ingredient (E) (e.g., Eudragit) and the ingredient (F) (e.g., triacetin) are substantially immiscible with the ingredient (A) and are added to form a matrix for the micro particles and to impart a sustained-releasing property to the active ingredient stably contained in the micro particles. Particularly, when the composition contacts with water or saliva, the ingredient (F) in the matrix is gradually replaced with water. As water penetrates the matrix and eventually reaches the micro particles containing the active ingredient (D), the active ingredient (D) dissolves into water and is released from the micro particles.

The process for preparing the pharmaceutical composition is next described.

In the first step of the process, the ingredient (A) and the ingredient (B) are mixed to obtain a first mixture. In one embodiment, the first mixture containing the ingredient (A) and ingredient (B) is heated so that the ingredient (B) is completely dissolved in the ingredient (A). In another embodiment, substantially all water contained in the first mixture is removed, e.g., by heating the mixture preferably under a reduced pressure. Any suitable mixing means can be used. In one embodiment, "mixing" is achieved by stirring. Usually the first step is carried out at a temperature to not lower than about 80° C., preferably to about 90° C. to about 100° C. and under a reduced pressure of not higher than about 100 mmHg, preferably not higher than about 80 mmHg. When the temperature is lower than about 80° C., not all of the ingredient (B) can dissolve into the ingredient (A). On the other hand, when the pressure is not reduced to not higher than about 100 mmHg, it becomes difficult to remove substantially all water from the first mixture.

The phrase "removing substantially all water" as used herein means that the amount of water contained in a mixture becomes not greater than about 5% by weight, preferably not greater than about 3% by weight, and more preferably not greater than about 1% by weight, based on the total weight of the mixture.

Preferably, the amount of water contained in the first mixture may be calculated by measuring the amount of trapped water which has been removed, e.g., by suction, and subtracting the measured amount from the amount of water contained in the first mixture before suction. Thereby, the amount of water contained in the first mixture may be accurately calculated.

In one embodiment, the blending ratio of the ingredient (B) is about 2 parts to about 11 parts by weight, preferably about 4 parts to about 9 parts by weight and more preferably about 6 to 8 parts by weight, per 100 parts by weight of the ingredient (A).

Next, the ingredient (C) is mixed with the first mixture to obtain a second mixture. Depending upon the kind of the ingredient (A) contained in the first mixture, it may be difficult in some cases to uniformly mix the ingredient (C), if added alone, with the first mixture even at a high temperature (e.g., 140° C. and above). In such case, the ingredient (C) may be added to the first mixture after being dispersed in a polyhydric alcohol at ambient temperature. This polyhydric alcohol may be the same or different from the ingredient (A) contained in the first mixture.

In one embodiment, the blending ratio of the ingredient (C) is about 2 parts to about 11 parts by weight, preferably about 4 parts to about 8 parts by weight and more preferably about 5 parts to about 6 parts by weight, per 100 parts by weight of the ingredient (A).

In another embodiment, the blending ratio of the ingredient (B) is about 0.3 parts to about 3.5 parts by weight, preferably about 0.5 parts to about 2.5 parts by weight and more preferably about 0.7 to 1.5 parts by weight, per 1 part by weight of the ingredient (C).

Then, the second mixture containing the ingredients (A), (B) and (C) is heated to about 95° C. to about 180° C., preferably about 100° C. to about 140° C. When the temperature of the second mixture is lower than about 95° C., it becomes difficult to dissolve the ingredient (C) completely.

On the other hand, when the temperature of the second mixture is higher than about 180° C., degradation of the ingredient (C) may occur and, thereby, the active ingredient (D) cannot be stably formulated in the pharmaceutical composition. In one embodiment, this step is conducted under the atmospheric pressure or a reduced pressure. When the mixing is conducted under the atmospheric pressure, denaturation of the ingredients, such as degradation of the ingredient (C), can be suppressed because the condition becomes milder than that under a reduced pressure. On the other hand, when the mixing is conducted under a reduced pressure, additional water can be removed from the mixture during mixing. Preferably, the step is conducted under the atmospheric pressure, followed by under a reduced pressure. Thereby, not only the ingredient (C) can be mixed mildly with the first mixture under the atmospheric pressure, but also bubbles in the second mixture can be removed simultaneously with removal of water under a reduced pressure and, thereby, stability of the pharmaceutical composition can be further enhanced.

In an embodiment, the second mixture is subjected to a reduced pressure after dissolution of the ingredient (C) is confirmed. An extent of a reduced pressure may be properly set, and it is preferably not higher than about 100 mmHg, more preferably not higher than about 80 mmHg. Moreover, reduction of the pressure may be initiated at an initial temperature not lower than about 65° C., preferably not lower than about 80° C. and, thereafter, the temperature may be lowered to not higher than about 75° C., preferably not higher than 65° C. while the pressure is reduced.

In one embodiment, substantially all water in the second mixture is removed prior to mixing with the active ingredient (D). Further, from the viewpoint of stability of the ingredient (C), removal of water under a reduced pressure is preferably conducted on the first mixture before mixing the first mixture and the ingredient (C).

After it is confirmed that the ingredient (C) has been uniformly dissolved in the second mixture, the weight-average molecular weight Mw of the ingredient (C) in the second mixture is measured, for example, by gel permeation chromatography. In one embodiment, the molecular weight of the water-soluble polymer in the second mixture is from about 150,000 to about 300,000, more preferably from about 170,000 to about 285,000. Typically, Mw of the ingredient (C) in the second mixture is 20 to 30% less than Mw of the ingredient (C) prior to being mixed with the first mixture due to cleavage of the ingredient (C) caused by the elevated temperatures.

Next, the temperature of the second mixture is maintained at not higher than about 75° C., preferably not higher than about 70° C., and more preferably not higher than about 65° C., and not lower than about 30° C., and more preferably not lower than about 35° C. The second mixture is then mixed with the active ingredient (D), hydrophobic ingredient (E) and amphipathic ingredient (F) for a period of T minutes. When the temperature is higher than about 75° C., degradation of the active ingredient (D) may occur and a potency of the pharmaceutical composition is decreased. In one embodiment, the mixture is preferably degassed under a reduced pressure preferably not higher than about 100 mmHg, more preferably not higher than about 80 mmHg. Further, when the mixture is not degassed, stability of the pharmaceutical composition is decreased.

T refers to the mixing time when all the ingredients (A) to (F) are present. In one embodiment, T satisfies the equation: $0.00136M-287<T<0.00136M-161$. In another embodiment, T satisfies following Equation I:

$$0.00136M-230<T<0.00136M-169 \qquad \text{Equation I}$$

In one embodiment, T is in a range of about 30 minutes to about 180 minutes. In another embodiment, T is in a range of about 30 minutes to about 90 minutes.

The mixing may be performed in any appropriate equipment. In one embodiment, the mixing is performed in a circular pot with a stirring device. The pot may have a diameter of about 350 mm and a depth of about 300 mm. The stirring device may be a stirring rod with one or more stirring blades at one end. The revolution speed can be about 5 to 60 rpm.

In one embodiment, the active ingredient (D), either alone or after being dissolved in a polyhydric alcohol which may be the same or different from the ingredient (A) used in the first mixture, is mixed with the second mixture at a temperature at about 60° C. to about 70° C. Thereafter, the resultant mixture is cooled to about 30° C. to about 35° C., to which the ingredients (E) and (F) are added. Preferably, the ingredient (E) is first dissolved in the ingredient (F) prior to the addition.

In one embodiment, the amount of the ingredient (B) is about 0.5 fold to about 10 fold by weight based on the weight of the active ingredient (D). When the amount of the ingredient (B) is within the range, the active ingredient (D) can be formulated with stability in the pharmaceutical composition. Preferably, the amount of the ingredient (B) is not lower than about 1 fold or about 2 fold and not higher than about 8 fold or about 5 fold by weight based on the weight of the active ingredient (D). In one embodiment, the amount of the ingredient (B) is about 2.5 fold by weight based on the weight of the active ingredient (D).

In an embodiment, a blending ratio of the ingredients (E) and (F) is about 1 part to about 100 parts by weight per 100 parts by weight of the sum of the ingredients (A), (B), (C) and (D). Within this blending ratio, the particle diameter of the micro particles may be controlled in a desirable range. Preferably, the blending ratio of the ingredients (E) and (F) is not lower than about 8 parts or about 12 parts by weight and not higher than about 25 parts or about 20 parts by weight, per 100 parts by weight of the sum of the ingredients (A), (B), (C) and (D).

In another embodiment, the blending ratio of the ingredient (F) is preferably 1.5 to 10 fold, more preferably 3.5 to 7 fold, and most preferably 6 fold relative to the ingredient (E). When this blending ratio becomes great, the particle diameter of the micro particles becomes large. Moreover, the release rate of the active ingredient from the micro particles becomes greater with increase in the particle diameter. It is believed that when the particle diameter of the micro particles is increased, a viscoelasticity of the pharmaceutical composition becomes lower and retention of the pharmaceutical composition at an administered portion is reduced. When the blending ratio is not within the above range, stability of the matrix deteriorates and sustained release of the active ingredient becomes difficult.

In one embodiment, the resultant pharmaceutical composition includes micro particles formed by the ingredients (A), (B), (C) and (D), which are dispersed in a matrix formed from the ingredients (E) and (F). In one embodiment, the micro particles have an average particle diameter of about 0.5 μm to about 1.2 μm. Preferably, the particle diameter is not smaller than about 0.7 μm or about 0.8 μm, and not larger than about 1.0 μm or about 0.9 μm.

In another embodiment, the pharmaceutical composition described herein is substantially free from water. An amount of water contained in the pharmaceutical composition is preferably not greater than about 5% by weight, more preferably not greater than about 3% by weight, and more preferably not greater than about 1% by weight, based on the total weight of the pharmaceutical composition. When the amount of water is greater than about 5% by weight, a potency of the active ingredient (D) cannot be maintained for a long period of time.

Furthermore, in addition to the ingredients (A) to (F) described above, the pharmaceutical composition described herein may optionally contain other ingredients conventionally used in pharmaceutical compositions, such as coloring agents, flavoring agents, surface active agents, excipients, so long as they does not deteriorate the effects of the pharmaceutical composition.

In one embodiment, the pharmaceutical composition has a viscoelasticity (tan δ) of about 0.35 to about 0.60 measured at 2 Hz. Preferably, the viscoelasticity is not lower than about 0.44 or about 0.45 and not higher than about 0.55 or about 0.53.

In another embodiment, the pharmaceutical composition has a release rate at 7 hours of about 40% to about 90%. More preferably, the release rate at 7 hours is not lower than about 50% or about 55%, and not higher than about 80% or about 70%.

The pharmaceutical composition described herein can be administered externally, particularly, onto a mucous membrane. For example, in the case where minocycline or a pharmaceutically acceptable salt thereof is used as the active ingredient, it may be produced into a dental pharmaceutical composition. The dental pharmaceutical composition may be produced as a pasty ointment pharmaceutical composition which is administered topically. In this case, it may be conveniently administered to an affected portion such as a periodontal pocket with a syringe for use in application for periodontal diseases. Further, occurrence of a systemic side effect which has been previously observed upon oral administration, for example, a digestive system side effect such as anorexia, nausea and diarrhea, a biochemical side effect such as thrombocytopenia and eosinophilia, or superinfection can be suppressed and a medicinal effect can be efficiently exerted. Moreover, by sustained-releasing of minocycline for a long period of time, re-administration of the pharmaceutical composition to a patient within a short period becomes un-necessary and a burden on the patient is reduced.

Next, the invention will be illustrated in more detail referring to working examples, which are intended to illustrative, and should not be construed to limit the scope of the invention.

All the references cited herein and in the examples that follow are expressly incorporated herein by reference in their entireties.

Example 22 (Micro Particles Formulation)

11.2 kg of glycerin was placed in a 20 L planetary mixer equipped with a vacuum pump, and 1 kg of magnesium chloride hexahydrate was dispersed therein. The mixer has a diameter of 350 mm and a depth of 300 mm. The revolution speed was 55 rpm. The mixture was heated to 90-100° C. at 100 mmHg and stirred for 60 minutes, to dissolve magnesium chloride hexahydrate in glycerin, as well to remove substantially all water contained in glycerin and magnesium chloride hexahydrate. Removed water was captured with a trap, and an amount thereof was measured. After the mixture was returned to the atmospheric pressure, another mixture in which 0.8 kg of hydroxy ethylcellulose (HEC) had been dispersed in 2.8 kg of glycerin was added to the mixture. This mixture was heated to 135° C. and stirred for 30 minutes until uniform dissolution of hydroxy ethylcellulose was visually observed. The mixture was cooled and an aliquot was removed for measurement of molecular weight Mw of hydroxy ethylcellulose contained in this intermediate product. The measured molecular weight was 212251.

The mixture was then degassed under a reduced pressure at 100 mmHg. After the temperature of the mixture became 65° C., a mixture in which 0.4 kg of minocycline hydrochloride had been dispersed in glycerin (the sum of weight equal to that of water trapped, 1 kg (the sum of weight was adjusted so that the total amount of the final product became 20 kg)) was added, followed by stirring. After uniform dissolution of minocycline hydrochloride was confirmed by visual observation, a solution in which 0.4 kg of Eudragit®RS had been dissolved in 2.4 kg of triacetin was added. Thereafter, the mixture was degassed and stirred uniformly for 60 minutes to obtain a paste-like pharmaceutical composition containing minocycline hydrochloride as an active ingredient in micro particles (Composition 1).

Measurement of Molecular Weight by Gel Permeation Chromatography

Measuring Equipment: Agilent 1260 Infinity II HPLC System

Preparation of Moving Phase:

0.1M of $NaNO_3$ was prepared and degassed by 30 min sonication.

Preparation of Samples:

1. Pullulan (reference) was prepared with a concentration between 0.1 to 0.2% (w/v).

2. 0.08 g of a sample was diluted with 1 ml of the moving phase and mixed well by vortex mixer and sonication.

3. Solution of step 2 is filtered with Millex-HP 13 mm PESO 0.45 µm.

4. 0.02 g of hydroxyethyl cellulose (raw material) was dissolved in 5 ml of the moving phase and mixed and filtered in the same manner as steps 2 and 3.

5. Shodex STANDARD P-82 was used as standard for the calibration curve.

Measurement of Molecular Weight:

Molecular weight was measured with following conditions:

Column: Shodex OHpakSB-806M HQ

UV detector: 210 nm

Flow rate: 0.5 ml/min

Temperature: 50° C.

Injection: 40 µl

Measurement of Particle Diameter Distribution

The particle size in Composition 1 was measured by a laser diffraction particle size analyzer (e.g., Shimadzu SALD-2200). Specifically, a blank measurement was first made. Then, a small amount of composition was placed on the glass slide and covered with a cover slip and pressed lightly so that the composition was stretched thinly. The glass slide was set in the measuring section and a neutral density (ND) filter was attached so that the absorbance was 1.0 or less and the maximum light intensity was about 30 to 60%. The measurement was carried out under the following conditions.

Bending rate: 1.60-0.10i where "i" means an angle of incidence.
Number of measurements: 1
Particle size range for evaluation: 0.03 to 280.00
The results are shown in FIG. 1.

As apparent from FIG. 1, the mean particle diameter (D50%) of Composition 1 is 1.0969 μm.

Microscopic Observation

Figure 2:
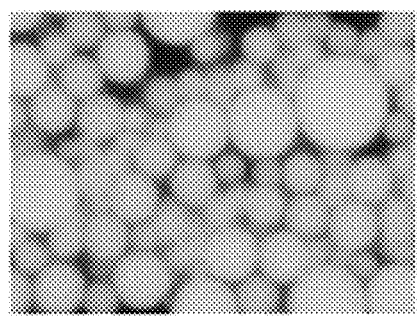
FIG. 2 is a scanning electron microphotograph showing a pharmaceutical composition including fluorescent micro particles in an embodiment.

Composition 1 diluted with triacetin was observed with a fluorescent microscopy. Emission of the micro particles was observed due to minocycline hydrochloride under the fluorescent light. This confirms the presence of minocycline hydrochloride in the micro particles (FIG. 2).

Measurement of Release Rate by Elution Test

Figure 3:
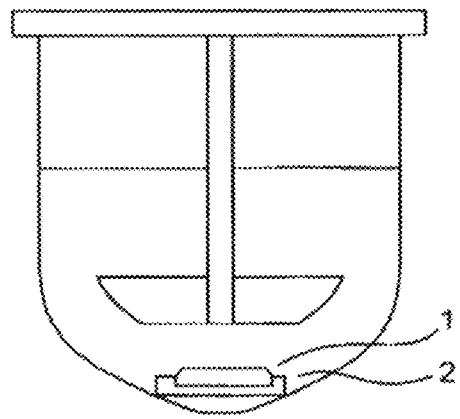
FIG. 3 is a schematic diagram illustrating a vessel used in an embodiment.

An elution test was performed according to a test method of Japanese Pharmacopoeia, Elution method, Second method with partial modification. That is, about 500 mg of a sample (1) was filled into a cell having an inner diameter of 30 mm and a depth of 0.5 mm (2) in place of a sinker, and the cell was immersed in the vessel (FIG. 3). Next, 500 ml of water was added and mixed with rotation at 100 rpm, 37° C. The concentration of minocycline hydrochloride eluted was calculated by measuring an absorbance at 348 nm with a spectrophotometer (Shimadzu Corporation, UV-260).

Figure 4:
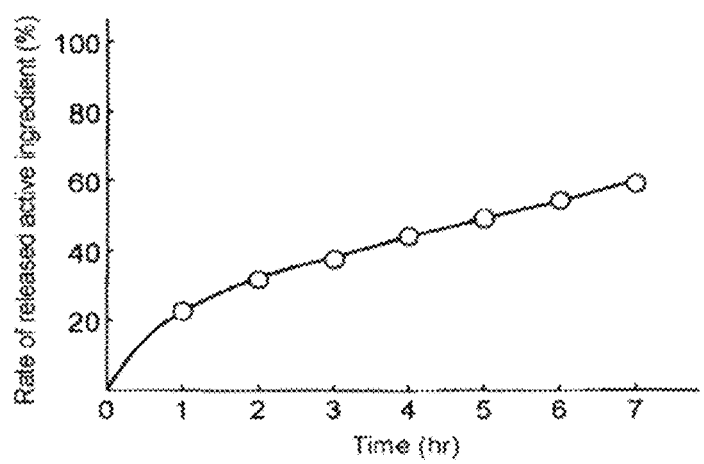
FIG. 4 is a graph showing the results of an elution experiment in an embodiment.

As apparent from the results shown in FIG. 4, Composition 1 shows a suitable release behavior and it is demonstrated that the active ingredient may be sustainedly-released by 20-40% at 3 hours and 50-60% at 7 hours.

Examples 1-21 and 23-25

Figure 5:
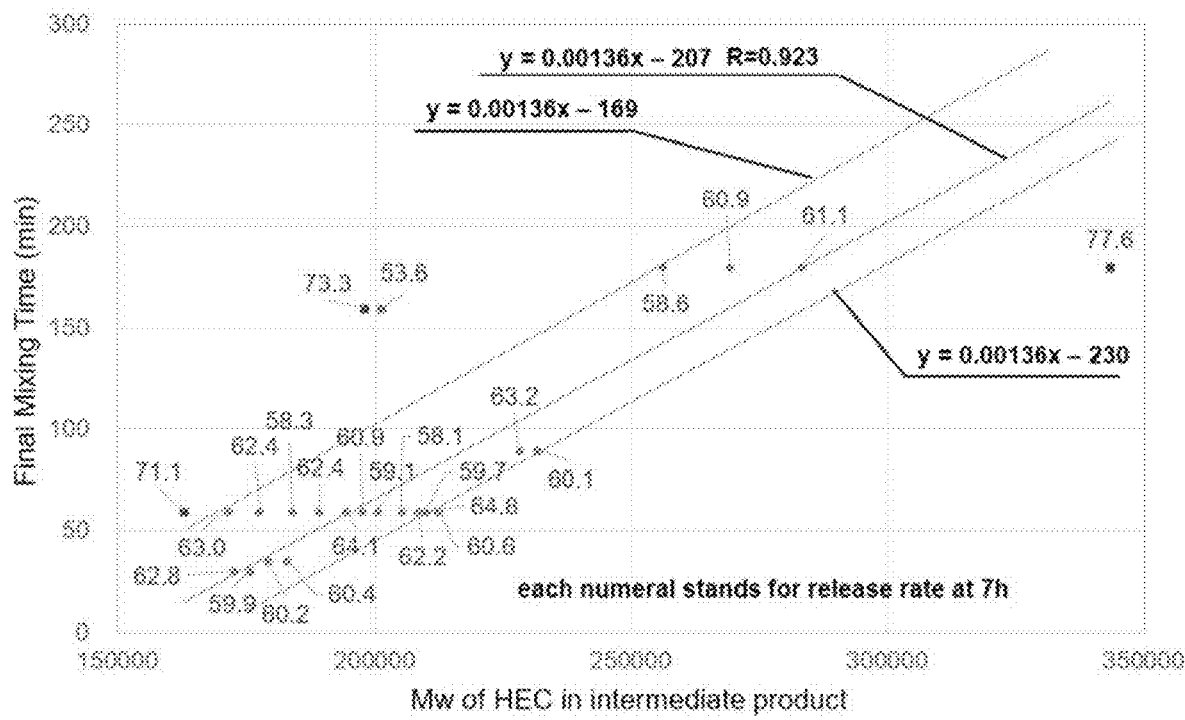
FIG. 5 is a plot of final mixing time T vs. molecular weight M of HEC in the first mixture of Examples 1-25.

Examples 1-21 and 23-25 were prepared in the same manner as the process of Example 22 except that HEC raw material having a different molecular weight was used and a corresponding fixing time was applied, as shown in Table 1. The plot of final mixing time vs. molecular weight of HEC in the intermediate product is shown in FIG. 5.

TABLE 1

|  | Mw of HEC (raw material) | Mw of HEC in intermediate product | Final mixing time (min) | Average of 7 h release rate (%) |
|---|---|---|---|---|
| Example 1 | — | 201110 | 160 | 53.6 |
| Example 2 | — | 205156 | 60 | 58.1 |
| Example 3 | 690373 | 184129 | 60 | 58.3 |
| Example 4 | — | 255886 | 180 | 58.6 |
| Example 5 | — | 200452 | 60 | 59.1 |
| Example 6 | — | 209987 | 60 | 59.7 |
| Example 7 | 433929 | 175832 | 30 | 59.9 |
| Example 8 | — | 231585 | 90 | 60.1 |
| Example 9 | — | 179458 | 35 | 60.2 |
| Example 10 | — | 183139 | 35 | 60.4 |
| Example 11 | 736062 | 212477 | 60 | 60.6 |
| Example 12 | — | 269331 | 180 | 60.9 |
| Example 13 | — | 197522 | 60 | 60.9 |
| Example 14 | — | 283319 | 180 | 61.1 |
| Example 15 | 736062 | 208398 | 60 | 62.2 |
| Example 16 | — | 177758 | 60 | 62.4 |
| Example 17 | — | 189126 | 60 | 62.4 |
| Example 18 | 418305 | 172427 | 30 | 62.8 |
| Example 19 | 434493 | 171382 | 60 | 63.0 |
| Example 20 | — | 227929 | 90 | 63.2 |

TABLE 1-continued

|  | Mw of HEC (raw material) | Mw of HEC in intermediate product | Final mixing time (min) | Average of 7 h release rate (%) |
|---|---|---|---|---|
| Example 21 | — | 194548 | 60 | 64.1 |
| Example 22 | — | 212251 | 60 | 64.8 |
| Example 23 | — | 162920 | 60 | 71.1 |
| Example 24 | — | 198047 | 160 | 73.3 |
| Example 25 | — | 343394 | 180 | 77.6 |

As shown in FIG. 5, when the mixing time T satisfies Equation I: $0.00136M-230 < T < 0.00136M-169$, a composition having a release rate at 7 h of 55% to 70% can be obtained.

Further, $T=0.00136M-207$, which is generated by linear approximation has a correlation coefficient R of 0.923 indicating strong positive correlation between M and T.

Example 111-139

Examples 111-139 were prepared in the same manner as the process of Example 22 except that HEC raw material having a different molecular weight was used and a corresponding fixing time, was applied, as shown in Table 2.

Viscoelasticity Measurement

Viscoelasticity (tan δ) was measured by frequency dependent measurement under the condition of 2 Hz frequency and 25° C. with rheometer (Anton Paar MCR102).
Measuring Apparatus: Rheometer MCR-102 (Anton Paar)
Measuring Cell: 125 mm parallel plate
Measuring Gap: 1 mm
Measurement Point: 16 points
Temperature: 25° C.
Frequency: 0.02 Hz-20 Hz
Strain Level: 1%

Figure 6:
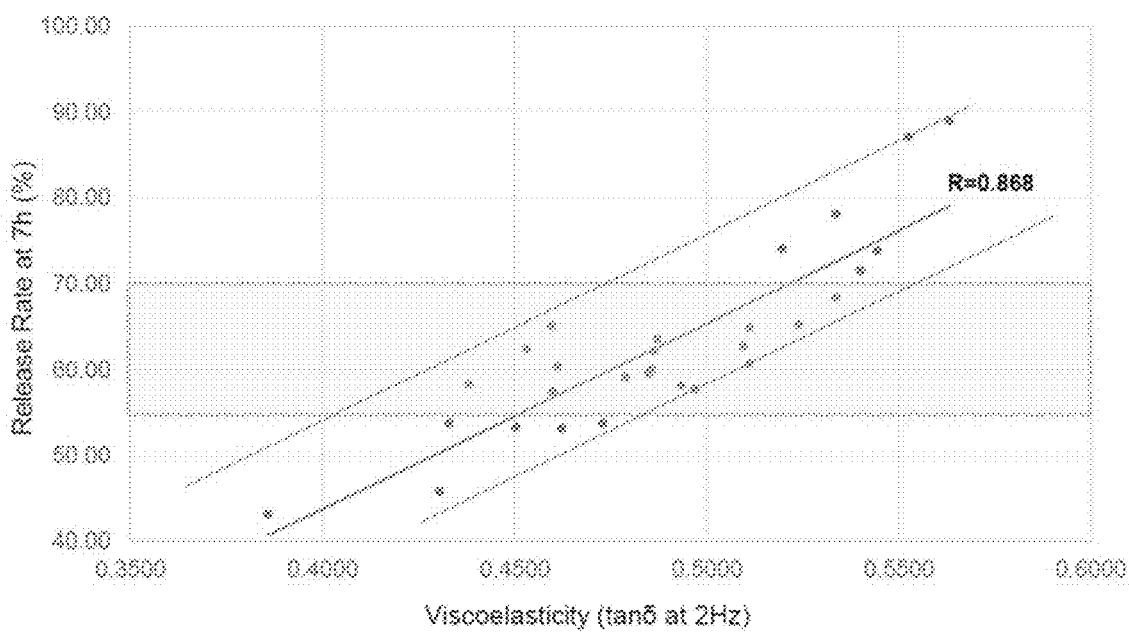
FIG. 6 is a plot of release rate at 7 h vs. viscoelasticity of the pharmaceutical compositions obtained in Examples 111-139.

The viscoelasticity and release rate of Examples 111-139 were measured and the results are summarized in Table 2. The plot of release rate vs. viscoelasticity of Examples 111-139 is shown in FIG. 6.

TABLE 2

Viscoelasticity of final products and release rates at 7 h

|  | Measured molecular weight of HEC in intermediate product | Final mixing time (min) | tanδ_2 Hz | Ave. of 1 h release (%) | Ave. of 7 h release (%) |
|---|---|---|---|---|---|
| Example 111 | 157140 | 60 | 0.3858 | 14.07 | 43.10 |
| Example 112 | 172427 | 60 | 0.4303 | 13.82 | 45.77 |
| Example 113 | 175832 | 45 | 0.4621 | 14.82 | 53.13 |
| Example 114 | 157140 | 30 | 0.4502 | 13.75 | 53.25 |
| Example 115 | — | 90 | 0.4730 | 14.83 | 53.73 |
| Example 116 | 157140 | 35 | 0.4327 | 13.38 | 53.73 |
| Example 117 | — | 90 | 0.4598 | 14.82 | 57.30 |
| Example 118 | — | 60 | 0.4969 | 17.50 | 57.65 |
| Example 119 | 196199 | 45 | 0.4933 | 16.63 | 58.08 |
| Example 120 | 175832 | 60 | 0.4379 | 13.80 | 58.25 |
| Example 121 | 172427 | 30 | 0.4788 | 16.72 | 59.07 |
| Example 122 | 211792 | 60 | 0.4848 | 17.60 | 59.52 |
| Example 123 | — | 60 | 0.4857 | 15.83 | 60.00 |
| Example 124 | 196199 | 60 | 0.4610 | 14.08 | 60.30 |
| Example 125 | — | 45 | 0.5111 | 17.28 | 60.70 |
| Example 126 | 175832 | 30 | 0.4862 | 17.52 | 62.18 |
| Example 127 | 172427 | 45 | 0.4530 | 14.87 | 62.42 |

TABLE 2-continued

Viscoelasticity of final products and release rates at 7 h

| | Measured molecular weight of HEC in intermediate product | Final mixing time (min) | tanδ_2 Hz | Ave. of 1 h release (%) | Ave. of 7 h release (%) |
|---|---|---|---|---|---|
| Example 128 | 211792 | 45 | 0.5095 | 19.08 | 62.70 |
| Example 129 | 170909 | 30 | 0.4871 | 17.57 | 63.57 |
| Example 130 | — | 60 | 0.5112 | 19.22 | 64.88 |
| Example 131 | 170909 | 45 | 0.4595 | 15.78 | 65.10 |
| Example 132 | 196199 | 30 | 0.5240 | 19.27 | 65.23 |
| Example 133 | — | 45 | 0.5337 | 20.48 | 68.38 |
| Example 134 | — | 30 | 0.5400 | 20.45 | 71.55 |
| Example 135 | — | 30 | 0.5444 | 22.85 | 73.87 |
| Example 136 | 217835 | 45 | 0.5197 | 20.78 | 74.12 |
| Example 137 | 211792 | 30 | 0.5337 | 22.60 | 78.07 |
| Example 138 | — | 30 | 0.5525 | 32.78 | 87.13 |
| Example 139 | 217835 | 30 | 0.5631 | 32.12 | 88.96 |

"—" indicates that value was not determined.

As shown in FIG. 6, when the viscoelasticity of the composition falls within the range of 0.44 to 0.55, a composition having a release rate at 7 h of 50% to 80% can be obtained. Further, when the viscoelasticity of the composition falls within the range of 0.45 to 0.53, a composition having a release rate at 7 h of 55% to 70% can generally be achieved.

The invention claimed is:

1. A process for preparing a pharmaceutical composition, the process comprising:
  i) heating a mixture comprising ingredients (A), (B) and (C) to a temperature of about 95° C. to about 180° C. to obtain an intermediate product, wherein the ingredient (C) is dissolved in the intermediate product, and the ingredient (C) in the intermediate product has a molecular weight M measured by gel permeation chromatography, wherein M is in a range from about 150000 to about 300000;
  ii) removing substantially all water in the intermediate product, and
  iii) mixing the intermediate product with a pharmaceutically active ingredient (D), a hydrophobic ingredient (E) and an amphipathic ingredient (F) at a temperature ranging from about 30° C. to 75° C. for a period of T minutes, thereby producing the pharmaceutical composition comprising micro particles dispersed in a matrix, wherein the micro particles comprise the ingredients (A), (B), (C) and (D); and the matrix comprises the ingredients (E) and (F), wherein:
  T satisfies: $0.00136M-230<T<0.00136M-169$;

wherein:
  (i) the ingredient (A) is glycerin, ethylene glycol or diethylene glycol;
  (ii) the ingredient (B) is a magnesium salt or hydrate thereof;
  (iii) the ingredient (C) is hydroxyethyl cellulose, hydroxypropyl cellulose, hydroxypropylmethyl cellulose, or polyvinylpyrrolidone;
  (iv) the ingredient (D) is a tetracycline, penicillin, carbapenem, cephem, monobactum, aminoglycoside or macrolide antibiotic; polyene, azole, echinocandin or pyrimidine antibiotic; steroid or non-steroid anti-inflammatory, or a pharmaceutically acceptable salt thereof;
  (v) the ingredient (E) is a copolymer of methyl methacrylate with butyl methacrylate and dimethylaminoethyl methacrylate, or a copolymer of ethyl acrylate with methyl methacrylate and methacrylate ethyl trimethylammonium chloride; and
  (vi) the ingredient (F) is triacetin, tributyrin, ethylene glycol diacetate, diethyl sebacate, diethyl phthalate, dibutyl phthalate, diisopropyl adipate, or dibutyl succinate;

wherein:
  (i) ingredient (A) is about 50% to about 85% by weight, based on a total weight of the pharmaceutical composition;
  (ii) ingredient (B) is about 0.5% to about 10% by weight, based on the total weight of the pharmaceutical composition;
  (iii) ingredient (C) is about 0.1% to about 20% by weight, based on the total weight of the pharmaceutical composition;
  (iv) ingredient (D) is about 0.1% to about 10.0% by weight, based on the total weight of the pharmaceutical composition;
  (v) ingredient (E) is about 0.5% to about 10% by weight, based on the total weight of the pharmaceutical composition; and
  (vi) ingredient (F) is about 5% to about 25% by weight, based on the total weight of the pharmaceutical composition;

wherein:
  (i) a blending ratio of the ingredient (B) to the ingredient (A) is about 2 parts to about 11 parts by weight, per 100 parts by weight of the ingredient (A);
  (ii) a blending ratio of the ingredient (C) to the ingredient (A) is about 2 parts to about 11 parts by weight, per 100 parts by weight of the ingredient (A);
  (iii) a blending ratio of the ingredient (B) to the ingredient (C) is about 0.3 parts to about 3.5 parts by weight, per 1 part by weight of the ingredient (C);
  (iv) an amount of the ingredient (B) is about 0.5 fold to about 10 fold by weight based on a weight of the ingredient (D);
  (v) an amount of the ingredient (F) is about 1.5 fold to about 10 fold by weight based on a weight of the ingredient (E); and
  (vi) a blending ratio of the ingredients (E) and (F) is about 1 parts to about 100 parts by weight, per 100 parts by weight of the ingredients (A), (B), (C) and (D);

wherein:
  the micro particles have an average diameter of about 0.5 µm to about 1.2 µm, and wherein:
  the pharmaceutical composition has a viscoelasticity of about 0.44 to about 0.55 by frequency dependent measurement.

2. The process of claim 1, wherein:
  (i) the ingredient (A) is glycerin;
  (ii) the ingredient (B) is magnesium chloride, magnesium gluconate, or a hydrate thereof;
  (iii) the ingredient (C) is hydroxyethyl cellulose or polyvinylpyrrolidone;
  (iv) the ingredient (D) is minocycline, doxycycline, tetracycline, oxytetracycline, chlortetracycline or a pharmaceutically acceptable salt thereof;
  (v) the ingredient (E) is a copolymer of ethyl acrylate with methyl methacrylate and methacrylate ethyl trimethylammonium chloride; or
  (vi) the ingredient (F) is triacetin.

3. The process of claim 1, wherein the intermediate product is a solution of the ingredients (B) and (C) dissolved in the ingredient (A).

4. The process of claim 1, wherein an amount of water contained in the intermediate product is not greater than about 5% by weight, based on a total weight of the intermediate product.

5. The process of claim 1, wherein the mixing iii) is performed at about 30° C. to about 70° C.

6. The process of claim 1, wherein the mixing iii) comprises:
  iii-1) mixing the intermediate product with the ingredient (D) to obtain an intermediate mixture; and
  iii-2) mixing the intermediate mixture obtained in iii-1) with the ingredients (E) and (F).

7. The process of claim 1, wherein T is in a range of about 30 minutes to about 90 minutes.

8. The process of claim 1, wherein an amount of water contained in the pharmaceutical composition is not greater than about 5% by weight, based on a total weight of the pharmaceutical composition.

9. The process of claim 1, wherein the pharmaceutical composition has an average release rate of about 55% to about 70% after 7 hours in an elution test.

\* \* \* \* \*